United States Patent [19]

Lemmey

[11] Patent Number: 4,915,626
[45] Date of Patent: Apr. 10, 1990

[54] DENTAL INSPECTION AND DISPLAY APPARATUS

[76] Inventor: Edgar S. Lemmey, 70 Westwood Dr., New York, N.Y. 11590

[21] Appl. No.: 298,466

[22] Filed: Jan. 18, 1989

[51] Int. Cl.[4] ............................................. A61C 3/00
[52] U.S. Cl. ...................................... 433/31; 433/29; 358/93; 350/640
[58] Field of Search ............... 433/29, 30, 31; 128/10, 128/11, 21; 350/640; 358/93, 98

[56] References Cited

U.S. PATENT DOCUMENTS

| | | | |
|---|---|---|---|
| 3,861,044 | 1/1975 | Swinson, Jr. | 433/213 |
| 3,884,222 | 5/1975 | Moore | 433/31 |
| 4,051,534 | 9/1977 | Dukich et al. | 358/93 |
| 4,184,175 | 1/1980 | Mullane, Jr. | 358/106 |
| 4,398,799 | 8/1983 | Swift | 358/93 |
| 4,468,197 | 8/1984 | Provost | 433/30 |
| 4,629,425 | 12/1986 | Detsch | 433/31 |
| 4,727,416 | 2/1988 | Cooper et al. | 433/29 |
| 4,757,381 | 7/1988 | Cooper et al. | 358/98 |

*Primary Examiner*—John J. Wilson
*Attorney, Agent, or Firm*—Darby & Darby

[57] ABSTRACT

A dental inspection apparatus to view an image of the interior of the mouth of a patient and contemporaneously display a video image of the interior of the mouth.

10 Claims, 1 Drawing Sheet

DENTAL INSPECTION AND DISPLAY APPARATUS

BACKGROUND OF THE INVENTION

This invention relates generally to dental inspection apparatus and more particularly to a device for viewing of areas within the mouth by direct observation of an image in a mirror as well as the contemporaneous video display and/or recordation of the image.

Although electronic video endoscopes have been used in recent years, such devices which generally include a light source, camera and lens, are inserted into the mouth. Such devices must comfortably fit into the mouth, and while in the mouth, be readily manipulated by dentists and dental surgeons. Thus, the more component elements that constitute the endoscopic portion of the device (that is to fit into and be manipulated within the mouth), the greater the degree of required miniaturization. Miniaturization of the component elements of dental endoscopic devices necessitates the use of nonstandard dental equipment which increases costs materially.

The need to miniaturize the endoscopic portion of the device to be inserted into the mouth, particularly the camera, may prohibit the use of other cameras possessing highly desirable features and capabilities which cannot be miniaturized cost effectively.

Sterilization of video endoscopes also becomes a potential problem due to the susceptibility of damage of delicate electrical, optical, or video elements if such elements cannot be or are not readily removed before being subjected to the high sterilization pressures and temperatures. Furthermore, the need to withstand the stresses and loading of repeated cycles of sterilization results in higher manufacturing costs.

U.S. Pat. Nos. 4,629,425, 3,884,222 and 4,727,416 disclose certain features relating to the field of the invention, but as will be discussed below, are not directed to nor do they suggest the present invention.

For several years it has been recognized that it is desirable to illuminate mirrors that are to be inserted into the mouth. One such dental mirror is set forth in U.S. Pat. No. 4,629,425. In this patent a dental mirror unit is disclosed that has provisions for cleaning the surface of the mirror with air and/or water without removing the mirror from the mouth and for illuminating the mirror surface with light from a fiber optic system. However this patent does not disclose any means for providing a video display and/or recordation of the image reflected by the mirror.

U.S. Pat. No. 4,727,416 discloses an electronic video dental camera having a camera head and appurtenances which are inserted into the mouth. The camera head includes fiber optic light guides and illumination lenses, as well as an image lens and sensor which is connected to a video control cable.

U.S. Pat. No. 3,884,222 discloses a pharynx inspection apparatus having a light reflecting mirror for reflecting light into the cavity to be inspected. Light reflected from the mirror is picked up by a fiber optic system for viewing or photographing. This patent relies upon the use of a mirror having an opening for the retransmitted light to pass through and onto a series of focusing mirrors and lenses which then directs the focused image to a fiber optic transmitting means. Each of these elements is attached to the mirror and is inserted into the mouth.

SUMMARY OF THE INVENTION

The present invention is intended to overcome the above discussed drawbacks and limitations of the prior art. In accordance with the present invention, a dental inspection apparatus is provided which enables the dentist or dental surgeon to view the interior of the mouth of a patient and contemporaneously to display an enlarged video image of the interior of the mouth. A light reflecting mirror is inserted into the mouth which reflects into the mouth light originating from outside of the mouth. The mirror also reflects an image of the mouth to a camera positioned outside of the mouth which converts the reflected image to an output signal representative of that image.

DETAILED DESCRIPTION

Figure 1:
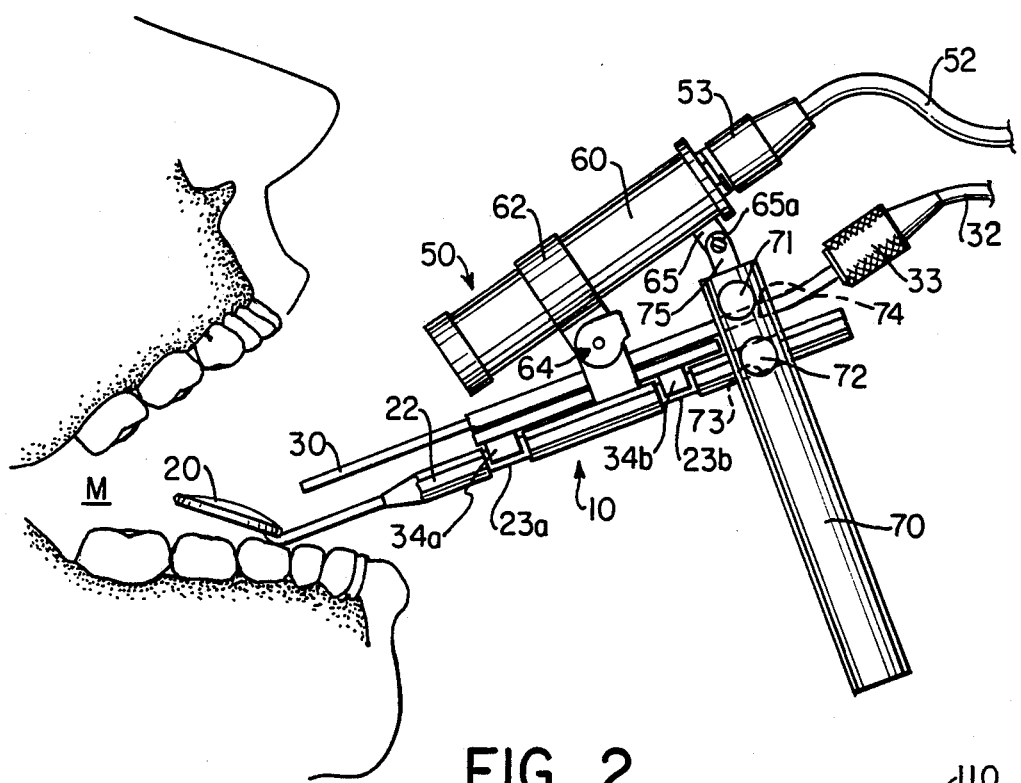
FIG. 1 is a side view of the dental inspection apparatus.
Figure 2:
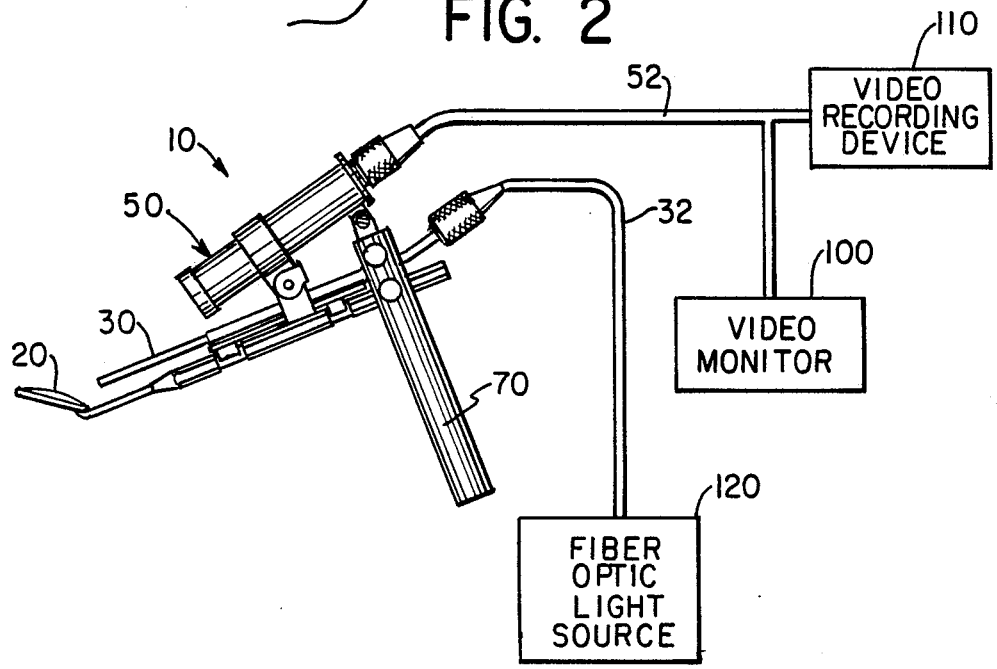
FIG. 2 is a schematic diagram showing the external light source and video monitor and recorder.

FIG. 1 shows the dental inspection device 10 which is to be held in one hand and includes inspection mirror 20, light guide 30, and mounting tube 60 in which is located micro camera 50. Inspection mirror 20 and a portion of fiber optic light guide 30 are shown within the mouth M of a patient. Light is carried through fiber optic cable 32 and into fiber optic light guide 30 from which it is reflected by inspection mirror 20 into the mouth M. Inspection mirror 20 reflects the image of a portion of the patient's mouth which is received by micro camera 50. The output signal of camera 50 is transmitted via camera cable 52 to a conventional video monitor 100 and/or conventional video recording device 110 shown in FIG. 2. Although direct electrical connections between the camera and the video recorder are shown, remote transmission devices could be used instead. Unlike typical endoscopic devices, the image reflected by mirror 20 can be directly observed without resort to viewing the image on the video monitor. Furthermore, while the dentist or dental technician holds the present invention in one hand, he can work in the patient's mouth with his free hand as well as simultaneously display the work being performed on the video monitor.

Inspection mirror 20 is rigidly mounted on handle 22 which is secured to handle 70 through aperture 73 and thumb screw 72. By releasing thumb screw 72, mirror handle 22 can be slid along as well as rotated around its longitudinal axis. Inspection mirror 20 which is rigidly attached to handle 22 will also rotate around the axis of mirror handle 22.

Fiber optic light guide 30 which directs light onto inspection mirror 20 is attached to handle 70 through aperture 74. Pivoting around its axis and longitudinal movement of light guide 30 is prohibited by clips 34a and 34b which clip onto recesses 23a and 23b formed along the periphery of mirror handle 22.

The intensity of light emanating from light guide 30 is controlled by a fiber optic light source (not shown) which is connected via fiber optic cable 32 to light guide 30 by connector 33.

Although not shown in the figures, means can be provided to cause a desired flow or stream of a selected fluid or gas over the mirror in order to defog and/or clean it in a conventional manner.

Mounting tube bracket 62 secures mounting tube 60 to fiber optic light guide 30 by swivel bracket 64. Swivel bracket 64 permits the angle between mounting tube 60 and light guide 30 to vary according to the angle of alignment with inspection mirror 20. The mounting tube is also attached to handle 70 by elevation stem 65 and mounting elevation rod 75 secured by pin 65a. The angle of alignment between camera 50 and the surface of mirror 20 is varied by sliding rod 75 within mounting tube bore 76 which extends longitudinally within handle 70. Once a desired angle of alignment is obtained by extending or withdrawing rod 75 from bore 76, it is secured by rotating thumb screw 71 to contact and press against rod 75.

Micro camera 50 is secured within mounting tube 60 outside the mouth, and thus does not become contaminated by the patient's saliva or blood.

However, inspection mirror 20, light guide 30, mounting tube 60 as well as other elements may become contaminated thus requiring sterilization. By removing camera 50 from tube 60, and disconnecting connector 53, camera cable 52, and connector 33, as well as fiber optic cable 32, all contaminated as well as potentially contaminated elements of the present invention can then be sterilized. Thus, delicate electrical, video and optical components need not be subjected to the cyclical and damaging temperatures and pressures associated with sterilization.

While the present invention has been particularly shown and described with reference to a preferred embodiment thereof, it will be understood by those skilled in the art that various changes in form and details may be made therein without departing from the spirit and scope of the invention.

What is claimed is:

1. An apparatus for viewing the interior of the oral cavity of a patient and contemporaneously providing a signal for displaying a video image of the oral cavity on a video monitor comprising:
   (a) a light reflecting mirror for insertion into the mouth, said mirror having a light reflecting surface for directing light into the mouth from a source of light located outside of the mouth and for reflecting from within the mouth an image of the mouth;
   (b) a handle adapted to be held outside of the mouth for holding and manipulating said mirror into a selected position;
   (c) a mirror mounting means to mount the mirror on the handle;
   (d) a camera for receiving the reflected image from the reflecting surface and for converting said image to an output signal representative of the reflected image adapted to being coupled to a video monitor; and
   (e) a camera mounting means for securing the camera to the handle such that the camera is positioned physically remote from said reflecting surface and does not extend into the mouth of the patient.

2. An apparatus for viewing as in claim 1 further including a lighting means located outside of the mouth for illuminating the interior of the oral cavity.

3. An apparatus for viewing as in claim 2 further including light-directing means connected to the handle for directing light from said lighting means onto the light reflecting surface of the mirror.

4. An apparatus for viewing as in claim 3 wherein the light directing means is a fiber optic line.

5. An apparatus for viewing as in claim 4 further including a video monitor responsive to said output signal.

6. An apparatus for viewing as in claim 4 further including a video recorder responsive to said output signal.

7. An apparatus for viewing as in claim 4 wherein the light-directing means is affixed to the mirror mounting means and the handle.

8. An apparatus for viewing as in claim 7 wherein the camera mounting means includes a camera mounting tube in which the camera is placed and a camera mounting tube bracket which is affixed to the mounting tube and the light directing means.

9. An apparatus for viewing as in claim 1 further including a camera aligning and positioning means for selectively aligning and positioning the camera at an angle relative to the reflective surface.

10. An apparatus for viewing as in claim 8 wherein the camera aligning and positioning means includes (i) a swivel bracket which connects the camera mounting bracket to the light directing means and (ii) a mounting elevation means connected at a first end to the camera mounting tube and at another end to the handle.

* * * * *